US010004251B2

(12) United States Patent
Muñoz Moreno et al.

(10) Patent No.: US 10,004,251 B2
(45) Date of Patent: Jun. 26, 2018

(54) BIOLOGICAL DEGRADATION OF OCHRATOXIN A INTO OCHRATOXIN α

(75) Inventors: María Rosario Muñoz Moreno, Madrid (ES); Héctor Rodríguez López, Madrid (ES); Blanca De Las Rivas González Del Ray, Madrid (ES); Inés María Reverón Poján, Madrid (ES); Emilia Garcia Moruno, Asti (IT); Francesca Doria, Asti (IT); Antonella Costantini, Asti (IT)

(73) Assignee: CENTRO DI RICERCA PER L'ENOLOGIA (CRA-ENO), Asti (IT)

( * ) Notice: Subject to any disclaimer, the term of this patent is extended or adjusted under 35 U.S.C. 154(b) by 573 days.

(21) Appl. No.: 13/812,549

(22) PCT Filed: Jul. 28, 2011

(86) PCT No.: PCT/ES2011/070557
§ 371 (c)(1),
(2), (4) Date: Apr. 5, 2013

(87) PCT Pub. No.: WO2012/025657
PCT Pub. Date: Mar. 1, 2012

(65) Prior Publication Data
US 2013/0209609 A1 Aug. 15, 2013

(30) Foreign Application Priority Data
Jul. 29, 2010 (ES) .................................. 201031188

(51) Int. Cl.
A23L 3/365 (2006.01)
A23L 3/3571 (2006.01)
C12P 17/06 (2006.01)
A23K 10/18 (2016.01)
A23L 5/20 (2016.01)
A23L 29/00 (2016.01)
C12R 1/13 (2006.01)

(52) U.S. Cl.
CPC ............ *A23L 3/3571* (2013.01); *A23K 10/18* (2016.05); *A23L 5/28* (2016.08); *A23L 29/065* (2016.08); *C12P 17/06* (2013.01); *C12R 1/13* (2013.01)

(58) Field of Classification Search
CPC .............................. A23L 1/0158; C12P 17/06
See application file for complete search history.

(56) References Cited

PUBLICATIONS

Hwanga, et al.,Journal of Food Protection®, No. 5, May 1994, pp. 365-444, pp. 410-414(5).*
Amezqueta, Food Control, vol. 20, Issue 4, Apr. 2009, pp. 326-333.*
Juhasz,Canadian Journal of Microbiology, 1990, 36(7): 510-512, 10.1139/m90-089.*

(Continued)

*Primary Examiner* — Donald Tarazano
*Assistant Examiner* — Philip Dubois
(74) *Attorney, Agent, or Firm* — RatnerPrestia (57) ABSTRACT The invention relates to the use of a microorganism of the genus *Brevibacterium* for the biological degradation of ochratoxin A, in which the microorganism is preferably *Brevibacterium casei, Brevibacterium linens, Brevibacterium iodinum* or *Brevibacterium epidermidis*. In addition, the invention relates to a method for the production of ochratoxin α using said microorganism.

8 Claims, 5 Drawing Sheets (56) References Cited

PUBLICATIONS

Amezqueta et al., "Ocratoxin A decontamination: A review," Food Control 20 (2009) 326-333.
Hwang et al., "Degradation of Ochratoxin A by *Acinetobacter calcoaceticus*," Journal of Food Protection, vol. 57, No. 5, pp. 410-414.
Juhasz et al., "Purification and characterization of an extracellular proteinase from Brevibacterium linens," Canadian Journal of Microbiology, 1990, 36(7): 510-512. Abstract.
Varga et al., "Degradation of ochratoxin A by *Aspergillus* species," Intl. Journal of Food Microbiology 59 (2000) 1-7.
Bejaoui et al., "Biodegradation of ochratoxin A by *Aspergillus* section Nigri species isolated from French grapes: a potential means of ochratoxin A decontamination in grape juices and musts," FEMS Microbiol Lett 255 (2006) 203-208.
Abrunhosa et al., "Biodegradation of Ochratoxin A by Fungi Isolated from Grapes," J. Agric. Food Chem. 2002, 50, 7493-8496.
Rodriguez et al., Degradation of Ochratoxin A by *Brevibacterium* Species, Journal of Agricultural and Food Chemistry, 2011, 59, pp. 10755-10760.

\* cited by examiner

BIOLOGICAL DEGRADATION OF OCHRATOXIN A INTO OCHRATOXIN α

CROSS REFERENCE TO RELATED APPLICATIONS

This application is the U.S. National Phase Application Of PCT/ES2011/070557, filed Jul. 28, 2011, which claims priority to Spanish Application No. P201031188, filed Jul. 29, 2010, the contents of such applications being incorporated by reference herein.

The invention relates to the use of a microorganism of the genus *Brevibacterium* for the biological degradation of ochratoxin A, preferably the microorganism is *Brevibacterium casei*, *Brevibacterium linens*, *Brevibacterium iodinum* or *Brevibacterium epidermidis*. In addition, the invention relates to a method for producing ochratoxin α by using said microorganism.

BACKGROUND ART

Mycotoxins are secondary metabolites produced by numerous mold species, principally belonging to the genera *Penicillium*, *Aspergillus* and *Fusarium*. Currently, more than 300 mycotoxins are known, including, among others, the aflatoxins, ochratoxins, trichothecenes, fumonisins, zearalenone, citrinin and patulin. Although the acute and subacute toxicity of some mycotoxins is well known, the effects of long-term ingestion is of greater concern, as the small quantities ingested with foods on a continual basis accumulate in the body and can have, in some cases, mutagenic and carcinogenic effects (Martin et al., 1990. Revista de Agroquímica y Tecnología de los Alimentos, 30:315-332).

Ochratoxins are a group of mycotoxins produced on different substrates by some species of fungi, noteworthy among them are the genera *Aspergillus* and *Penicillium*. Although there are various types of ochratoxins, ochratoxin A (OTA) is the most toxic. Because these molds are capable of growing in a wide variety of foods, OTA can be found in meat and dairy products, cocoa, fruit, cereals, coffee, olive oil, nuts, spices, baby food and fermented products such as wine and beer among others, under highly variable humidity, pH and temperature conditions (Engelhardt G. et al., 1999. Adv. Food Sci. 21, pp. 88-92; Romani S., et al., 2000. Journal of Agricultural and Food Chemistry 48, pp. 3616-3619).

OTA is a derivative of isocoumarin linked to L-β-phenylalanine through the carboxyl group. Chemically, it is N-[(5-chloro-3,4-dihydro-8-hydroxy-3-methyl-1-oxo-1H-2-benzopyran-7-yl)carbonyl]-L-phenylalanine, a chlorinated dihydrocoumarin linked via a carboxyl group by an amide bond to a L-β-phenylalanine molecule. Other types of ochratoxins are ochratoxin B (OTB), a less toxic, nonchlorinated derivative of OTA, ochratoxin C (OTC), OTA ester, with little toxic potential, ochratoxin α (OTα) and ochratoxin β (OTβ), hydrolysis products of OTA and OTB that do not have the phenylalanine molecule and are not considered toxic, respectively (Pavón et al., 2007. RCCV Vol. 1 (2)).

In recent years, ochratoxins and in particular ochratoxin A, have received particular attention, due to their high toxicological potency. Ochratoxin A, which is noticeably nephrotoxic, has been related to serious illnesses, such as "Balkan endemic nephropathy" or urinary tract tumors in humans and "spontaneous nephropathy in pigs" or "avian nephropathy" in animals. In addition, studies carried out with animals and in human cell lines have revealed its carcinogenic, genotoxic, immunotoxic, hepatotoxic, neurotoxic and teratogenic properties (Kuiper-Goodman, T. 1996. Food Addit. Contam. 13, pp. 53-57) and it has been detected in human blood after the intake of foods contaminated with it (Petkova-Bocharova, T. et al., 1988. Food Addit.Contam. 5, pp. 299-301).

Therefore, in order to ensure the health of consumers exposed to this mycotoxin, the European Union has established limits for the OTA concentration allowed in cereals, raisins, roasted coffee whether beans or ground, instant coffee, wines and grape musts, and spices. The limits vary according to the raw material, but are within a range of 2-10 µg/kg. In the case of dried vine fruits the maximum level is 10 µg/kg and the limit for unprocessed cereals is 5 µg/kg, whereas for processed cereal products used for direct human consumption it is 3 µg/kg. However, a limit of less than 0.5 µg/kg has been established for cereal-based processed foods when such foods are intended for infants and young children (European Commission Regulation (EC) No 1881/2006 of 19 Dec. 2006). The World Health Organization (WHO), on its part, has proposed 5 µg/kg as the maximum limit for OTA in cereals.

For spices and licorice, Regulation (EU) No 105/2010 establishes temporarily and for the first time a maximum content of ochratoxin A, which enters into effect this July and will be stricter as of 2012. In the case of spices the maximum concentration of 30 µg/kg is established from 1 Jul. 2010 to 30 Jun. 2012, and 15 µg/kg as of 1 Jul. 2012. The spices considered are: *Capsicum* spp. (fruit from such genus whether dry, whole or pulverized, including chili peppers, chili powder, cayenne and paprika), *Piper* spp. (fruit, including white and black pepper), *Myristica fragrans* (nutmeg), *Zingiber officinale* (ginger), *Curcuma longa* (turmeric), and spice blends containing one or more of the aforementioned spices.

Due, therefore, to the fact that OTA is a real problem in the food sector due to its toxicity and high presence in a large number of foods and beverages, it is necessary to reduce the levels of this mycotoxin present in food products. In this context, reliable methods capable of degrading this mycotoxin are sought.

In the coffee industry, for instance, solvent decaffeination has been reported to significantly reduce OTA levels (Heilmann W. et al., 1999. Eur. Food Res. Technol. 209, pp. 297-300); in addition, the use of ozone treatments is also proposed as a detoxification method for OTA-contaminated beans (McKenzie K. S. et al., 1997. Food Chem. Toxicol. 35, pp. 807-820). Additionally, various studies have been carried out in wine cellars to reduce the presence of OTA in wine musts and wines, among them being different decontamination procedures based on physical-chemical elimination of the toxin (Castellari M. et al., 2001. J. Agric. Food Chem. 49, pp. 3917-3921; Dumeau F., and Trioné D., 2000. Rev. Fr. Oenol. 95, pp. 37-38; García-Moruno E. et al., 2005. Am. J. Enol. Vitic. 56, pp. 73-76).

The use of physical or chemical methods for mycotoxin decontamination can eliminate, besides mycotoxin, many substances important from the organoleptic or nutritional point of view. Therefore, methods for the biological degradation of toxins are currently a very promising approach.

Regarding the biological decontamination of OTA, the scientific literature contains reports of enzymes with carboxypeptidase A (CPA) activity, such as bovine pancreatic CPA (Sigma), capable of degrading OTA. These enzymes hydrolyze the amide bond in the OTA molecule to yield L-phenylalanine and ochratoxin α (OTα) (Pitout M. J. 1969. Biochem Pharmacol 18, pp. 485-491).

It was later reported that some microorganisms have a similar mechanism of action in OTA degradation to that used by CPA enzymes, such as *Phenylobacterium immobile* (Wegst W. and Lingens F. 1993. FEMS Letters 17, pp. 341-344), *Acinetobacter calcoaceticus*, (Hwang C. A., and Draughon F. A. 1994. J. Food Prot. 57, pp. 410-414) or *Aspergillus niger* (Abrunhosa L. and Venancio A. 2007. Biotechnol. Lett. 29, pp. 1909-1914). It is also known that some strains of *Rhodococcus* are able to degrade a wide variety of organic compounds, such as *Rhodococcus erythropolis* which has recently been seen capable of degrading aflatoxin B1, a mycotoxin that is structurally different from OTA. (Teniola O. D. et al., 2005. Int. J. Food Microbiol. 105, pp. 111-117).

However, although the results obtained have important implications for food safety, none of the microorganisms mentioned in the preceding paragraph and able to degrade OTA are used in the food industry.

Therefore, although different treatments based on physical, chemical and biological methods to decrease ochratoxin A levels have been described, until now none of the treatments described can be used for OTA detoxification of foods.

Physical-chemical washes, treatments with absorbent materials, solvent extraction, etc., are among the physical-chemical processes commonly used. These methods are costly and may also eliminate various nutrients or compounds that are important from an organoleptic point of view. Furthermore, no biological treatments used to lower OTA content in foods, beverages and animal feeds are currently in existence, as none of the microorganisms that have been described and capable of degrading OTA are related to foods.

Consequently, there is a manifest difficulty with finding a suitable method for ochratoxin A degradation in food products such that the food properties are unaltered from both the organoleptic and nutritional point of view.

DESCRIPTION OF THE INVENTION

The invention relates to the use of a microorganism of the genus *Brevibacterium* for the biological degradation of ochratoxin A. In addition, the invention relates to the use of said microorganism for the production of ochratoxin α that proceeds from the biological degradation of ochratoxin A. This microorganism can be used for the biological degradation of ochratoxin A in food products.

The invention provides a method for biologically degrading ochratoxin A by *Brevibacterium* to yield OTα, a product not toxic to ruminants (Kiessling et al., 1984. Applied and Environmental Microbiology, 47(5): 1070-1073) or in other mammals (*Application for the Approval of the use REGE-NASURE® Non-Shellfish Glucosamine Hydrochloride from Aspergillus niger (RGHAN), for use in Certain Foods Products under Regulation (EC) No 258/97 for the European Parliament and of the Council of 27 Jan. 1997 concerning novel foods and novel food ingredients. FINAL NON-CONFIDENTIAL 4 Aug. 2006*).

It is noteworthy that the invention has studied the potential of different strains belonging to the genera *Pseudomonas, Brevibacterium* and *Rhodococcus*. However, although all strains tested have proven activity in the degradation of organic compounds, such as *Rhodococcus erythropolis* which, as mentioned earlier, is capable of degrading aflatoxin B1, a mycotoxin that is structurally different from OTA, throughout the invention (Example 1, Table 1) it is shown that, of all tested strains, only those belonging to the genus *Brevibacterium* are capable of degrading OTA, said activity being a common characteristic of all strains belonging to said genus.

The genus *Brevibacterium* is included among the *Actinobacteria*, Gram-positive bacteria that although it includes species isolated from the soil, most species of this genus have been isolated from milk and cheeses, such as, but without limitation, *B. linens, B. casei* and *B. iodinum* which are used in the food industry for applications such as flavor formation, surface coloring and ripening of various kinds of cheese.

Therefore, the invention describes a method suitable for degrading ochratoxin A in food products such that the food properties are unaltered from both the organoleptic and nutritional point of view. In addition, it has been confirmed that degradation of this mycotoxin by the use of *Brevibacterium* leads to the synthesis of ochratoxin α. Based on all of the foregoing, the invention provides a method for the biological OTA detoxification and OTα synthesis in foods by using microorganisms of the genus *Brevibacterium*.

Therefore, the invention provides a solution to the state of the art for the problem of ochratoxin A degradation in food products by a biological method, that respects the organoleptic and nutritional characteristics of the food, based on the use of a microorganism belonging to the genus *Brevibacterium*, widely used in the cheese industry, a microorganism not previously related to ochratoxin degradation.

Thus, a first aspect of the invention relates to the use of a microorganism of the genus *Brevibacterium* for the biological degradation of ochratoxin A. The microorganism is selected, but without limitation, from among the list comprising preferably microorganisms of the species *Brevibacterium casei, Brevibacterium linens, Brevibacterium iodinum* or *Brevibacterium epidermidis*.

Hereinafter, in order to refer to any microorganism of the genus *Brevibacterium* the term "microorganism of the present invention" or "microorganism according to the invention" is used.

The term "biological degradation" refers to the transformation of a complex substance into another of simpler structure by microorganisms. As used in this description, the term biological degradation refers to the transformation of ochratoxin A by a microorganism according to the invention. The transformation of ochratoxin A leads to the appearance of other substances, such as, but without limitation, ochratoxin α. Ochratoxin A may be present in many types of substrates, such as, but without limitation, a food product, where said food product is, preferably, a cereal or a spice.

Another aspect of the invention relates to the use of the microorganism according to the invention, wherein biological degradation takes place in, at least, one food product.

The term "food product" as used in this description refers to all those substances or products of any nature, whether solid or liquid, natural or transformed, that, due to their characteristics, applications, components, preparation and state of conservation are susceptible to being commonly and ideally used for normal human or animal nutrition, as fruitful or diet products, in special dietary cases. As well as to all materials that are innocuous, in the absolute or relative sense, that, although with no nutritional value, can be used in food, whether human or animal. Preferably, the food product is intended for human use or animal use, and due to the fact that the highest contents of ochratoxin are found in cereals, the food product is preferably a cereal or a spice obtained from the plant selected from among the list comprising, but without limitation, *Capsicum* spp., *Piper* spp.,

*Myristica fragrans, Zingiber officinale* (ginger), *Curcuma longa* (turmeric), or any of their blends. In addition, the food product may be licorice.

Various studies (see, for example, Abrunhosa L. et al., 2002. J. Agric. Food Chem. 50, pp. 7493-7496) show that enzymatic hydrolysis of OTA with the enzyme CPA yields two compounds, one of which has a retention time near that of the OTα reference standard (obtained by acid hydrolysis of OTA).

Furthermore, the examples according to the invention show that the strains of *Brevibacterium* are not only capable of degrading OTA completely (see example 2) but that studies more specific with *B. casei* RM101 and B. linens DSM 20425$^T$ (see example 3) indicate also that both strains could grow in absence of glycerol in a culture medium containing OTA as sole, source of carbon. In addition, the OTα amounts detected in the supernatants of cultures in both strains, would correspond to the theoretical concentration produced by complete hydrolysis of OTA added to the medium (Example 3, Table 3).

From all these data it may be concluded that OTA hydrolysis can lead to L-phenylalanine and OTα, but L-phenylalanine released during the process may be used as a source of carbon during bacterial growth by corroborating that the various *B. linens* extracts tested contain an enzyme with carboxypeptidase activity and that, once it has hydrolyzed the amide bond of the OTA molecule yielding OTα and L-phenylalanine, other enzymes act on L-phenylalanines obtained by metabolizing them, thus explaining why only OTα is obtained in the examples of the invention.

Therefore, another aspect of the invention relates to the use of at least one biologically active molecule produced by the microorganism of the invention, for the biological degradation of OTA where preferably the biologically active molecule according to the above aspect is a protein capable of degrading OTA in, at least, OTα. This protein preferably is an enzyme with carboxypeptidase activity.

Hereinafter, to refer to any biologically active molecule produced by the microorganism of the invention, capable of degrading ochratoxin A in, at least, ochratoxin α according to the preceding paragraph, the term "molecule of the present invention", "molecule according to the invention", "protein of the present invention" or "protein according to the invention" can be used.

Although the genome of the *Brevibacterium linens* microorganism is not fully sequenced, there are already more than 50 proteins noted as having the function of "peptidases" of which 6 are carboxypeptidases with amino acid sequences defined by SEQ ID NO: 1, SEQ ID NO: 2, SEQ ID NO: 3, SEQ ID NO: 4, SEQ ID NO: 5 y SEQ ID NO: 6. Hence, the enzyme with carboxypeptidase activity as described in the preceding paragraph may have an amino acid sequence that is selected, but without limitation, from among the group comprising: SEQ ID NO: 1, SEQ ID NO: 2, SEQ ID NO: 3, SEQ ID NO: 4, SEQ ID NO: 5 or SEQ ID NO: 6.

Another aspect of the invention relates to the use of a composition comprising the microorganism of the present invention and/or the molecule of the present invention for the biological degradation of ochratoxin A.

Furthermore, due to the fact that, as already mentioned, the OTA degradation by *Brevibacterium* spp. bacteria observed in this study yields OTα (see example 3), another aspect relates to the use of the microorganism of the present invention, the molecule of the present invention, or the composition comprising the microorganism of the present invention or comprising the molecule of the present invention, or to the use of any one of the combinations of the preceding products, for producing OTα that proceeds from the biological degradation of ochratoxin A.

Another aspect of the invention relates to the method for the biological degradation of ochratoxin A, hereinafter "first method of the invention" comprising:
a. using at least one bacterium belonging to the genus *Brevibacterium*,
b. placing the bacterium from step (a) in contact with an aqueous solution and,
c. placing the product obtained in step (b) in contact with ochratoxin A.

In a preferred embodiment of the first method of the invention, the aqueous solution of step (b) allows the bacterium used in step (a) belonging to the genus *Brevibacterium* to survive.

In an even more preferred embodiment of the first method of the invention, the biological degradation of OTA yields OTα. And, in another even more preferred embodiment, the product in step (c) is placed in contact with a food product containing ochratoxin A, i.e., in step (c) the product obtained in step (b) is placed in contact with OTA through a food product containing this mycotoxin. The product of step (c) is preferably placed in contact with the food product by nebulization.

In a more preferred embodiment of the first method of the invention, the product obtained in step (c) is incubated at a temperature of between 10 and 50° C. for a period of between 1 hour and 20 days.

Another aspect of the invention relates to the method for the biological degradation of OTA, hereinafter "second method of the invention" comprising:
a. using at least one biologically active molecule or molecule of the invention, isolated from a bacterium belonging to the genus *Brevibacterium*,
b. placing the biologically active molecule obtained in step (a) in contact with ochratoxin A, and
c. incubating the product obtained in step (b) at a temperature of between 10 and 50° C. for a period of between 30 minutes and 30 days.
wherein the biological degradation of OTA according to the second method of the invention yields ochratoxin α.

In a preferred embodiment of the second method of the invention, the molecule in step (b) is placed in contact with a food product containing OTA, i.e., in step (b) the molecule obtained in step (a) is placed in contact with OTA through a food product containing this mycotoxin.

Throughout the description and the claims, the word "comprising" and its variants are not intended to exclude other technical properties, additives, components or steps. For a person skilled in the art, other items, advantages and characteristics of the invention may be learned in part from the description and in part from the practice of the invention. The following examples and figures are provided by way of illustration, and are not intended to be restrictive of the invention.

DESCRIPTION OF THE FIGURES

FIG. 1. Chromatogram of the analysis of the supernatant of *B. casei* RM101 cultured in basal salt medium without a source of carbon but with OTA (40 mg/L). Fluorimetric detector, $\lambda_{Ex}$ (excitation wavelength)=330 nm; $\lambda_{Em}$ (emission wavelength)=460 nm.

1A. Shows the supernatant at time 0 ($T_0$). Absorbance as measured in LU (luminescence units) is shown on the y-axis and time as measured in minutes (min) is shown on the x-axis.

1B. Shows the supernatant after 10 days of growth. The disappearance of the OTA peak and the appearance of the OTα peak can be observed. Absorbance as measured in LU (luminescence units) is shown on the y-axis and time as measured in minutes (min) is shown on the y-axis.

FIG. 2. UV/VIS (ultraviolet/visible) spectrum of OTα, in the supernatant of *B. casei* RM101 cultured in basal salt medium without a source of carbon but with OTA (40 mg/L).

2A. Shows the ochratoxin α spectrum obtained by diode array detector (DAD). Absorbance as measured in mAU (milli-absorption units) is shown on the y-axis and time as measured in minutes (min) is shown on the x-axis.

2B. Shows the ochratoxin α spectrum obtained by fluorimetric detector (FLD). Absorbance as measured in LU (luminescence units) is shown on the y-axis and wavelength as measured in nanometers (nm) is shown on the x-axis. Excitation wavelength (λex)=330 nm.

Ion abundance as measured is shown on the y-axis and mass-to-charge ratio (m/z) is shown on the x-axis.

EXAMPLES

The invention will be illustrated below by a series of assays performed by the inventors, which reveal that microorganisms belonging to the genus *Brevibacterium* are highly effective in transforming the mycotoxin OTA into OTα. It is shown how OTA is fully degraded by *Brevibacterium* and how said degradation leads to synthesis of OTα.

Additionally, due to increasing use of these microorganisms in the food industry, they are highly, recommendable for use in degrading OTA on foods potentially contaminated with this mycotoxin.

The following specific examples provided in this patent document serve to illustrate the nature of the present invention. These examples are only included for illustrative purposes and should not be interpreted as limitations to the invention claimed herein. Therefore, the examples described below illustrate the invention without limiting the field of application thereof. Furthermore, although the invention examples have used some specific strains belonging to *Brevibacterium*, these examples are only included for illustrative purposes and should not be interpreted as limitations of the invention claimed herein, the results being extrapolable to any bacterium of the genus *Brevibacterium* spp., and preferably to the species *Brevibacterium casei*, *Brevibacterium linens*, *Brevibacterium iodinum* or *Brevibacterium epidermidis*.

Example 1

Detection of the OTA Degradation Capacity of Various Strains of *Pseudomonas*, *Rhodococcus* and *Brevibacterium*

Due to the fact that soil bacteria are capable of transforming a wide variety of aromatic compounds, various species of *Actinobacterias* and *Pseudomonas* were initially cultured in liquid synthetic culture media such as BSM (basal salt medium) in the presence of OTA (10 μg/L).

1.1. Bacterial Strains Used and Bacteria Culturing.

In order to detect the capacity to degrade OTA, cultures of the strains *Rhodococcus erythropolis* CECT 3008, *Rhodococcus erythropolis* IGTS8, *Pseudomonas putida* DSMZ 291, *Pseudomonas putida* KT2442 and seven strains of various species of the genus *Brevibacterium* were used.

*Rhodococcus erythropolis* CECT 3008 (DSMZ 43060) was obtained from the Spanish Type Culture Collection (CECT). *Pseudomonas putida* DSM $291^T$ and six strains of *Brevibacterium* belonged to the German Collection of Microorganisms and Cell Cultures (DSMZ) (*Brevibacterium epidermidis* DSM $20660^T$, *Brevibacterium iodinum* DSM $20626^T$, *Brevibacterium linens* DSM $20425^T$, *Brevibacterium casei* DSM $20657^T$, *Brevibacterium casei* DSM 9657, *Brevibacterium casei* DSM 20658). The strain *Brevibacterium casei*, RM101, was isolated at the Institute of Industrial Fermentations IFI-CSIC, and was identified by 16S rDNA sequencing. *Rhodococcus erythropolis* IGTS8 and *Pseudomonas putida* KT2442 were supplied by Dr. Eduardo Diaz, of the CSIC Centre of Biological Research.

All bacteria were cultured in Luria-Bertani (LB) liquid medium supplemented with 0.5% glucose and incubated at 30° C. under aerobic conditions. For the OTA degradation assay, the bacteria were cultured in basal salt medium (BSM) containing 0.2% of glycerol, 4 g of $NaH_2PO_4-H_2O$, 4 g of $K_2HPO_4-31-120$, 2 g of $NH_4Cl$, 0.2 g of $MgCl_2-6H_2O$, 0.001 g of $CaCl_2-2H_2O$, and 0.001 g of $FeCl_3-6H_2O$ (Denome et al., 1994). Glycerol was not included in the experiments carried out to determine the potential use of OTA as a sole source of carbon by the bacteria analyzed.

1.2. OTA and OTα Reference Standard.

OTA in solid form was acquired from Sigma (Sigma-Aldrich) and diluted in 99% methanol under sterile conditions to yield a stock solution of 500 μg/mL. A reference standard solution of OTα (11.9 μg/mL) was also acquired from LGC Standards (Germany) and diluted 1:2 in acetonitrile to yield a reference standard solution of 5.9 μg/mL.

1.3. OTA Degradation Assay.

Initially, some strains of *Actinobacterias* (*Rhodococcus erythropolis* CECT 3008, *Rhodococcus erythropolis* IGTS8 and *Brevibacterium casei* RM101) and *Pseudomonas* (*P. putida* DSMZ $291^T$ and *P. putida* KT2442) were cultured in 25 mL of BSM medium spiked with OTA (approx. 10 μg/L) at 30° C. under aerobic conditions until the exponential phase of growth. The culture supernatants were analyzed by HPLC to determine the OTA concentration present.

In all degradation assays, the cells were separated from the supernatants by centrifuging at 3000×g for 10 min at 4° C. and the latter were analyzed by HPLC. In the case of *Brevibacterium*, settled cells were kept at −80° C. for successive analyses. Controls of BSM medium with OTA and without bacteria were also prepared.

1.4. HPLC and Mass Spectrometry Quantitation of OTA and OTα

The OTA concentration present in the supernatants, settled cells and settled cell wash solutions were quantitated according to the method disclosed in Del Prete V. et al., 2007. Journal of Food Protection, 70(9), pp. 2155-2160.

For the determination and quantitation of OTA, a Hewlett-Packard HPLC Model I, Series 1100, chromatograph (Hewlett-Packard, Palo Alto, Calif.), equipped with degasser, quaternary pump, autosampler, DAD detector and fluorescence detector (FLD) was used. An Alltima C18 (5 μm), 200 mm-4.6 mm column was used. The mobile phase was: eluent (A), acetonitrile; eluent (B), water (HPLC-grade)/acetonitrile/glacial acetic acid (89:10:1 v/v); eluent A:B=37:63 (v/v), in isocratic mode; flow rate, 1.3 mL/min; temperature, 30° C.; assay time, 20 min; FLD detector (λex=330 nm, λem=460 nm) and DAD detector (330 nm); injection volume, 100 μL. The detection limit for OTA under these conditions was 0.02 μg/L. The OTA reference standard was injected at two concentrations: 20 and 50 µg/L and the OTα reference standard was injected at a concentration of 5.9 mg/L. The samples, diluted in eluent A:B, were injected directly for analysis by HPLC.

The *Brevibacterium* settled cells were resuspended two times in 2 mL of absolute methanol for 1 hour to extract the OTA. After centrifuging at 3000×g for 15 min at 20° C., the supernatants were separated, collected in 5-mL vials and evaporated to dryness by nitrogen. To determine the OTA concentration, the dry residues were dissolved in HPLC mobile phase at the time of the chromatographic analysis.

For the mass spectrometry assay, a Hewlett-Packard Series 1100 MSD chromatograph (Palo Alto, Calif.) coupled to a quadrupole-mass detector with an electrospray ionization (ESI) interface was used. The separation was carried out by direct injection. The ESI parameters used were: N2 flow rate at 10 L/min, N2 temperature 330° C.; nebulizer pressure, 40 psi; capillary voltage, 4000 V. The ESI was operated in negative-ion mode, using a mass range of between m/z 100 and 800 and variable voltage ramping for fragmentation.

Table 1 lists the results obtained from the Actinobacterias and Pseudomonas species analyzed, capable of transforming a wide variety of aromatic compounds.

| Strains | OTA [µg/L] | Mean OTA [µg/L] | Decrease in OTA (%) |
|---|---|---|---|
| BSM + OTA (Control) | 11.06 | 11.01 | 0 |
| BSM + OTA (Control) | 10.96 | | |
| *Rhodococcus erythropolis* CECT 3008 (A) | 8.37 | 7.88 | 28.47 |
| *Rhodococcus erythropolis* CECT 3008 (B) | 7.38 | | |
| *Rhodococcus erythropolis* IGTS8 (A) | 9.50 | 8.81 | 19.98 |
| *Rhodococcus erythropolis* IGTS8 (B) | 8.12 | | |
| *Brevibacterium casei* RM101 (A) | n.d. | 0 | 100 |
| *Brevibacterium casei* RM101 (B) | n.d. | | |
| *Pseudomonas putida* DSM 291$^T$ (A) | 10.14 | 10.07 | 8.54 |
| *Pseudomonas putida* DSM 291$^T$ (B) | 10.00 | | |
| *Pseudomonas putida* KT2442 (A) | 7.72 | 8.18 | 25.70 |
| *Pseudomonas putida* KT2442 (B) | 8.64 | | |

The assays were performed two times (A) and (B);
n.d.: not detected;
$^T$type strain.

Table 1 lists the decrease in ochratoxin A (OTA) in BSM medium achieved by some species of *Actinobacterias* and *Pseudomonas*. The OTA concentration decrease observed is from 8 to 25% when analyzing the supernatants of cultures in the strains of *Rhodococcus erythropolis* and *Pseudomonas putida*. The small decrease observed appears to indicate that these bacteria have no OTA degradation mechanism and that OTA is likely adsorbed on the cell surface, in a similar manner to that described for lactic bacteria (Del Prete V. et al., 2007. Journal of Food Protection, 70(9), pp. 2155-2160) and yeasts (Cecchini F. et al., 2006. Food Microbiol. 23, pp. 411-417). Furthermore, in these strains the HPLC chromatographic analyses do not show the presence of OTA degradation products.

In the case of the strain *Brevibacterium casei* RM101, OTA disappeared completely from the culture supernatants.

Example 2

Degradation of OTA by *Brevibacterium*

Additional assays were performed using a larger number of *Brevibacterium* strains to confirm the observations with *B. casei* RM101 and to verify if this ability is a specific feature of the strain, species or genus being studied.

Additionally, in order to confirm the degradation of OTA by *Brevibacterium* spp., the strains were cultured in BSM medium with a four-fold concentration of OTA (40 µg/L). The *Brevibacterium* strains were cultured under aerobic conditions with agitation at 150 rpm for 10 days. These assays were performed in culture media containing OTA at a concentration of 40 µg/L. OTA levels equivalent to 40 µg/L are rarely found in foods or beverages. The degradation assays were performed as described in example 1.

TABLE 2

Decrease in ochratoxin A (OTA) in BSM medium achieved by *Brevibacterium*.

| Strains | OTA (µg/L)$^a$ | Decrease of OTA (%) |
|---|---|---|
| BSM + OTA (Control) | 39.81 | 0 |
| *Brevibacterium casei* DSM 20657$^T$ | n.d. | 100 |
| *Brevibacterium casei* DSM 9657 | n.d. | 100 |
| *Brevibacterium casei* DSM 20658 | n.d. | 100 |
| *Brevibacterium casei* RM101 | n.d. | 100 |
| *Brevibacterium linens* DSM 20425$^T$ | n.d. | 100 |
| *Brevibacterium iodinum* DSM20626$^T$ | n.d. | 100 |
| *Brevibacterium epidermidis* DSM 20660$^T$ | n.d. | 100 |

OTA (µg/L)$^a$ determined in the supernatants of three independent cultures;
n.d.: not detected;
$^T$type strain.

The OTA degradation assays show a complete disappearance of the toxin in all strains of the various *Brevibacterium* species analyzed. OTA added to the medium at a concentration of 40 µg/L was not detected by HPLC in any of the culture supernatants (Table 2). Nevertheless, after methanol extraction, the presence of OTA was also not detected in either the settled cells or the wash solutions.

These results corroborate the previous results and indicate that all *Brevibacterium* strains are capable of degrading OTA. The *Brevibacterium* genus comprises a heterogeneous group of nine coryneform species which are capable of degrading insecticides (DTT, DDE, etc.), as well as of producing extracellular proteases. These bacteria can be found in different habitats, including among them soil, poultry, fish, and human skin, and in foods.

Example 3

Mechanism of OTA Degradation by *Brevibacterium*

The strains *B. casei* RM101 and *B. linens* DSM 20425$^T$ were used, in order to confirm the capacity of these strains to degrade OTA at a higher concentration (40 mg/L), 1000-fold the concentration used in the previous assay, and to confirm the capacity of these strains to use OTA as a sole source of carbon. In this case the strains were cultured in BSM medium wherein glycerol (0.2%) and OTA (40 mg/L) were or were not present to thereby study the possible use of OTA as a sole source of carbon. The degradation assays were performed as described in example 1.

It has been possible to elucidate the mechanism of OTA degradation carried out by *Brevibacterium* spp. by analyzing the HPLC and mass spectrometry data of these strains, *B. casei* RM101 and *B. linens* DSM 20425$^T$.

TABLE 3

Decrease in ochratoxin A (OTA) and production of ochratoxin α (OTα) by *Brevibacterium casei* RM101 and *Brevibacterium linens* DSM 20425[T] in BSM medium with different composition.

| Strains | BSM medium with: | | Decrease in | | |
|---|---|---|---|---|---|
| | Glycerol (0.2%) | OTA (40 mg/L) | OTA (mg/L) | OTA (%) | OTα (mg/L) |
| B. casei RM101 | − | − | − | − | − |
| | + | − | − | − | − |
| | − | + | n.d. | 100 | 25.07 |
| | + | + | n.d. | 100 | 26.22 |
| B. linens DSM 20425 | − | − | − | − | − |
| | + | − | − | − | − |
| | − | + | n.d. | 100 | 26.19 |
| | + | + | n.d. | 100 | 26.79 | n.d.: not detected;
[T]type strain.

The results obtained (Table 3) again indicate that both *Brevibacterium* strains fully degrade the OTA present in the culture medium. The assay carried out using BSM medium without the traditional source of carbon (glycerol) showed that the strains *B. casei* RM101 and *B. linens* DSM 20425[T] are capable of using OTA as a sole source of carbon.

Figure 1A:
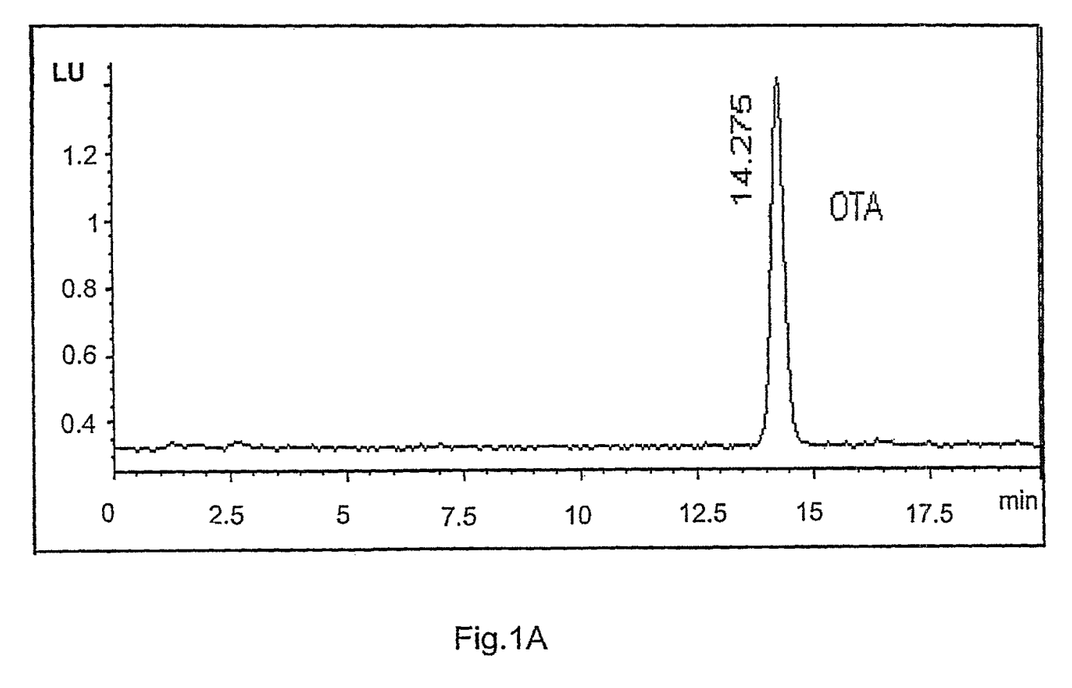
Figure 1B:
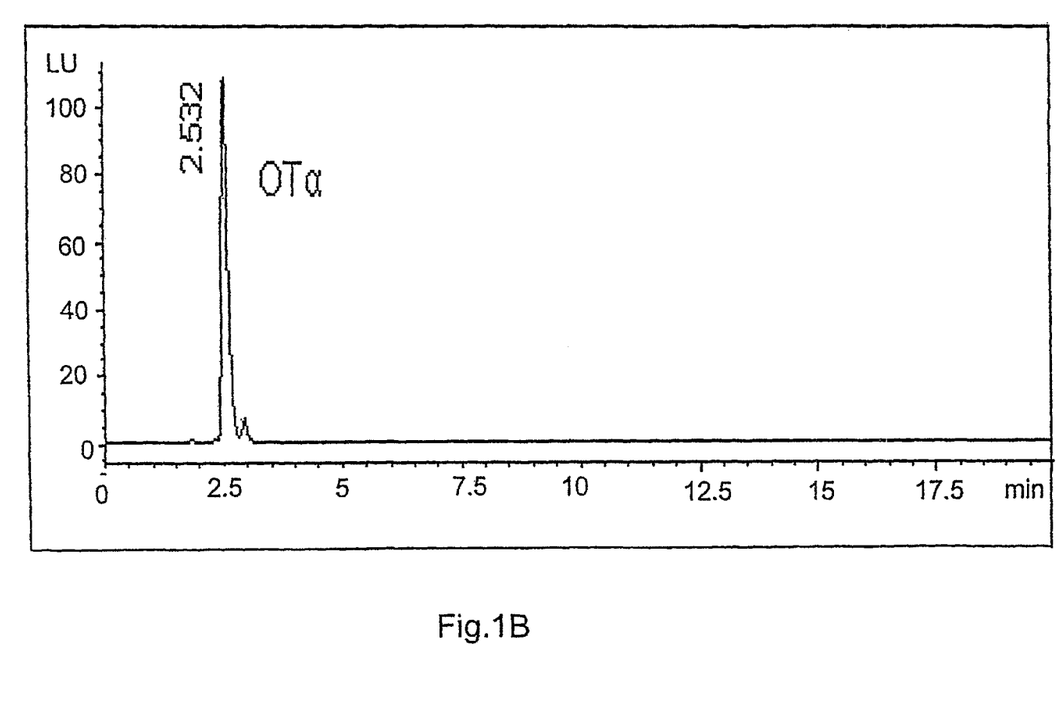
Figure 2A:
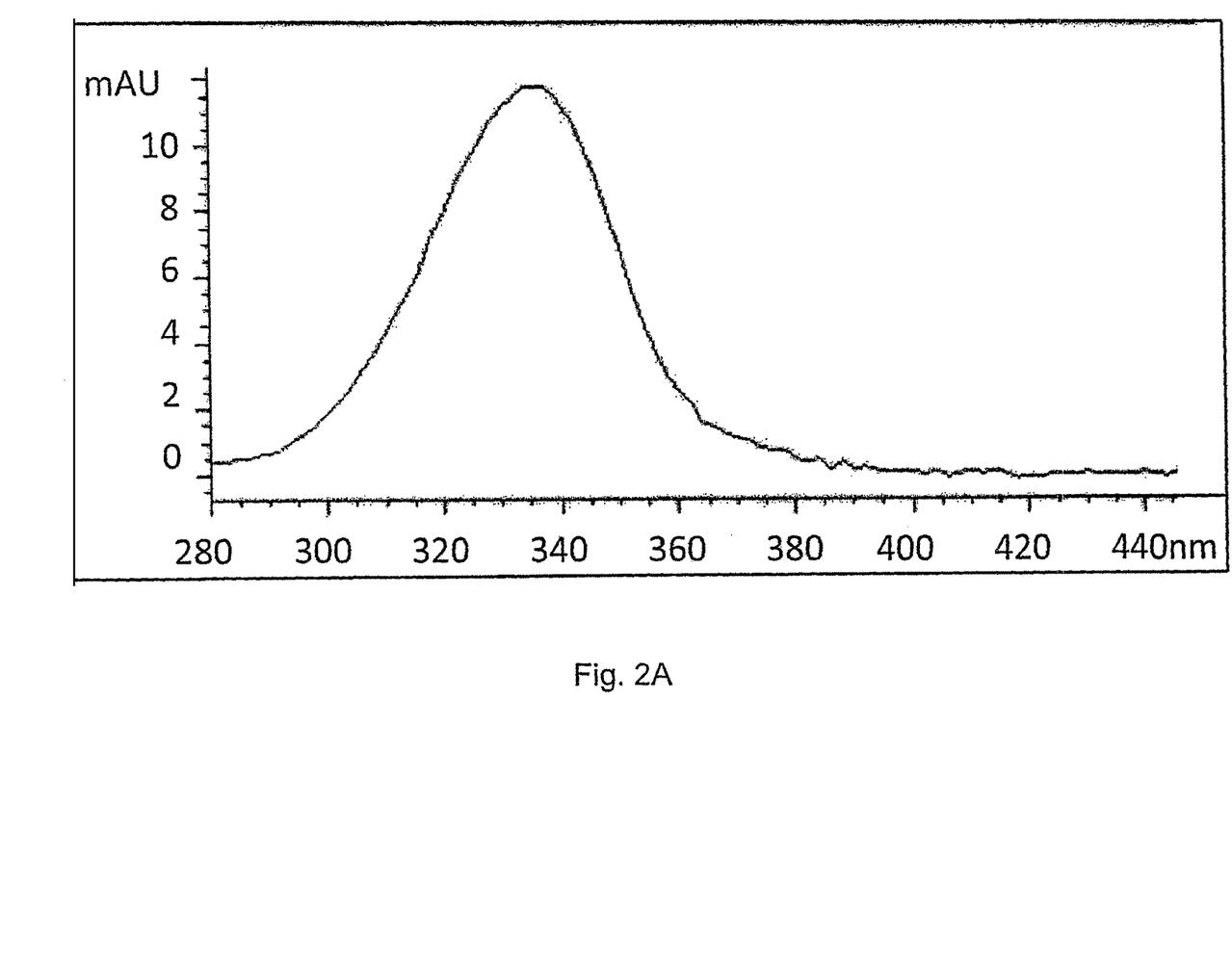
Figure 2B:
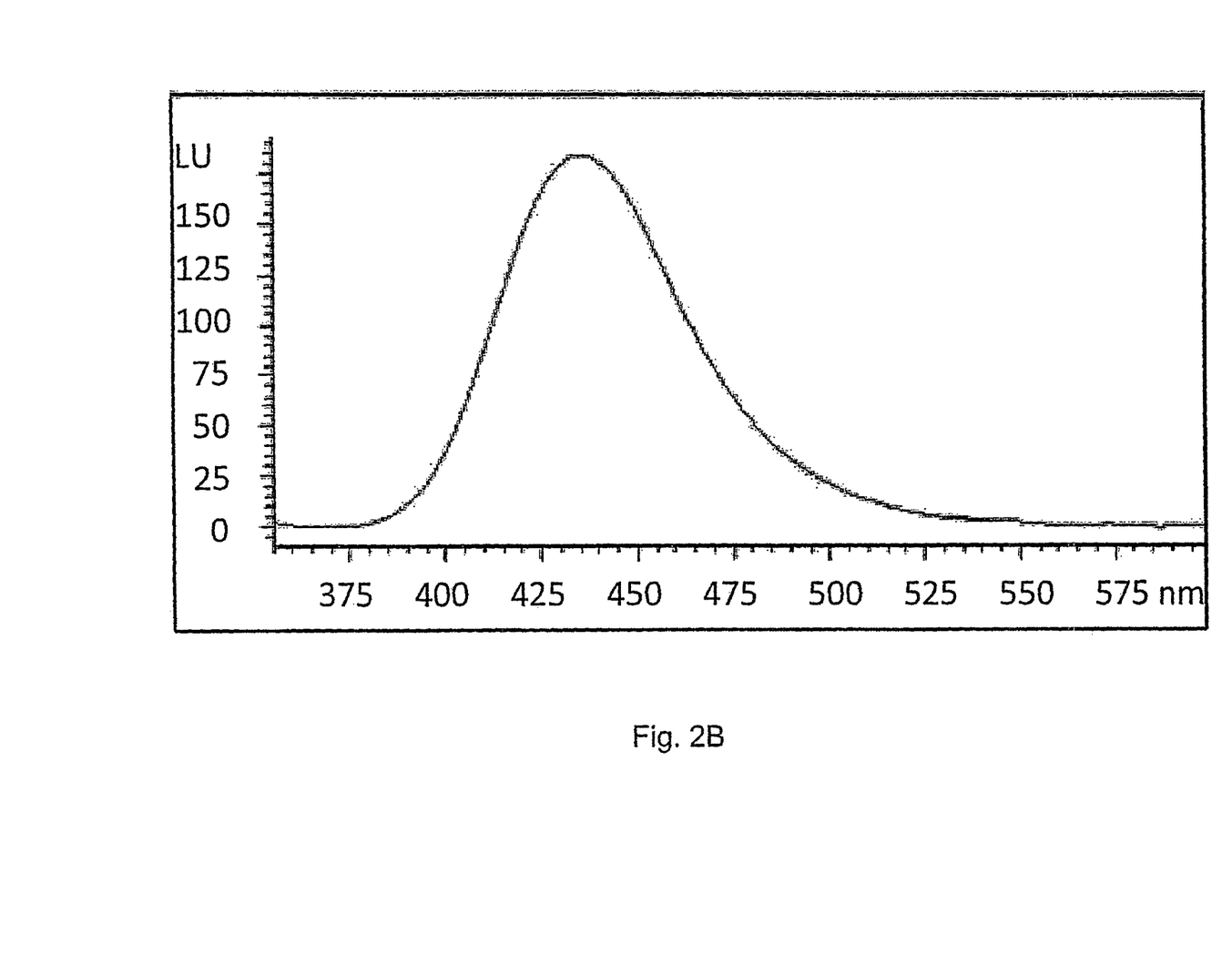
Figure 3:
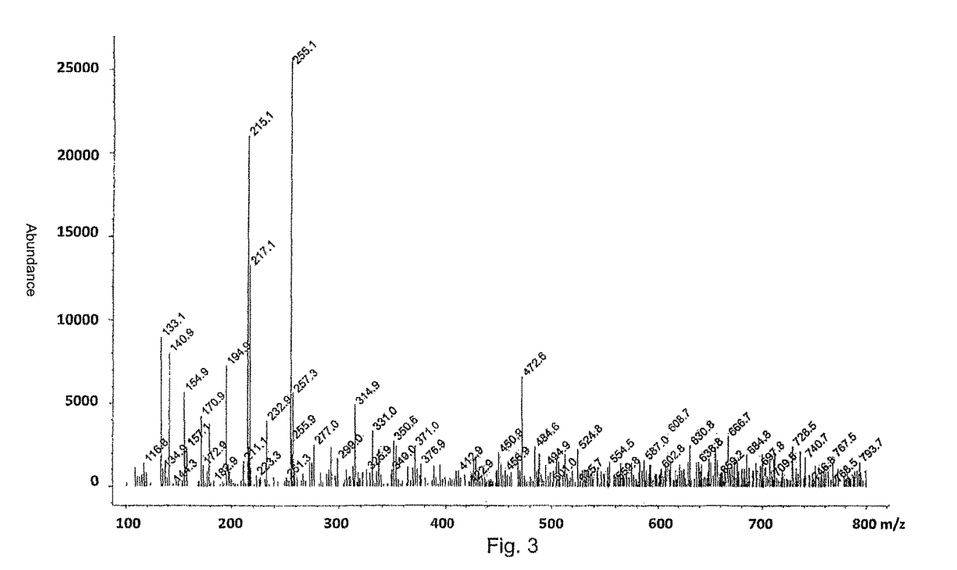
FIG. 3. Mass spectrum of OTα in the supernatant of *B. casei* RM101 cultured in basal salt medium without a source of carbon but with OTA (40 mg/L).

In parallel, an analysis of the respective chromatograms of the culture supernatants indicates the absence of the OTA peak and the appearance, in the elution profile, of a new peak with a different retention time and spectrum (FIG. 1). The amide bond present in OTA can be enzymatically hydrolyzed by a CPA to yield L-phenylalanine and OTα. The UV/VIS spectrum of the resulting compound (FIG. 2) is identical to the one seen in the reference standard corresponding to OTα. Furthermore, the results of the HPLC-MS assay make it possible to confirm the identity of the degradation product as OTα, given that a molecular ion peak [M-H]$^-$ was observed at m/z 255 in mass spectrometry (MW OTα=256) (FIG. 3).

The two *Brevibacterium* strains studied, *B. casei* RM101 and *B. linens* DSM 20425[T], were capable of growing in the absence of glycerol, as observed by increased cloudiness in the culture medium. In a culture medium containing OTA as a sole source of carbon, the bacterial population grew more slowly compared to the cultures grown in medium with glycerol and OTA; nevertheless, it should be mentioned that OTA was fully degraded in all cases. These results indicate the presence of a carboxypeptidase-type enzyme in *Brevibacterium* spp. strains, an enzyme that hydrolyzes the amide bond present in the OTA molecule. The L-phenylalanine released may be used as a source of carbon during bacterial growth. Table 3 shows the concentration of OTα recovered from the culture supernatants. The two strains studied, *B. casei* RM101 and *B. linens* DSM 20425[T], yield equivalent amounts of OTα regardless of whether the BMS medium contains glycerol or not. The OTα amounts detected correspond to the theoretical concentration produced by complete hydrolysis of OTA added to the medium.

The invention claimed is:

1. A method for the biological degradation of ochratoxin A, comprising:
 a. using at least one bacterium belonging to the genus *Brevibacterium* and selected from the group consisting of *Brevibacterium casei* DSM 20657, *Brevibacterium casei* DSM 9657, *Brevibacterium casei* DSM 20658, *Brevibacterium casei* RM101, *Brevibacterium linens* DMS 20425, *Brevibacterium iodinum* DSM 20626 and *Brevibacterium epidermidis* DSM 20660 in contact with an aqueous solution to obtain a first product, and
 b. placing the first product obtained in step (a) in contact with ochratoxin A to obtain a second product and incubating the second product at a temperature of between 10 and 50°C. for a period of between 1 hour and 20 days wherein the ochratoxin A is biologically degraded.

2. The method according to claim 1, wherein the aqueous solution of step (a) permits the survival of the bacterium.

3. The method according to claim 1, wherein the at least one bacterium belonging to the genus *Brevibacterium* is selected form the group consisting of *Brevibacterium casei* RM101 and *Brevibacterium linens* DSM 20425 and the biological degradation of ochratoxin A produces ochratoxin α.

4. The method according to claim 1, wherein the first product of step (a) is placed in contact with a food product containing ochratoxin A.

5. The method according to claim 4, wherein the first product of step (a) is placed in contact with the food product by nebulization.

6. A method for the biological degradation of ochratoxin A, comprising:
 a. placing a biologically active molecule in contact with ochratoxin A to obtain a product, wherein the biologically active molecule is an enzyme with peptidase activity produced by a microorganism belonging to the genus *Brevibacterium* and selected from the group consisting of *Brevibacterium casei* DSM 20657, *Brevibacterium casei* DSM 9657, *Brevibacterium casei* DSM 20658, *Brevibacterium casei* RM101, *Brevibacterium linens* DSM 20425, *Brevibacterium iodinum* DSM 20626 and *Brevibacterium epidermidis* DSM 20660; and
 b. incubating the product obtained in step (a) at a temperature of between 10 and 50° C. for a period of between 30 minutes and 30 days, whereby the ochratoxin A is biologically degraded.

7. The method according to claim 6, wherein the at least one bacterium belonging to the genus *Brevibacterium* is selected from the group consisting of *Brevibacterium casei* RM101 and *Brevibacterium linens* DSM 20425 and the biological degradation of ochratoxin A produces ochratoxin α.

8. The method according to claim 6, wherein step (b) the biologically active molecule is placed in contact with a food product containing ochratoxin A.

* * * * *

SEQUENCE LISTING

<160> NUMBER OF SEQ ID NOS: 6

<210> SEQ ID NO 1
<211> LENGTH: 390
<212> TYPE: PRT
<213> ORGANISM: Brevibacterium linens

<400> SEQUENCE: 1

```
Met Thr Thr Ser Gln Thr Ser Asp Leu Gln Ser Ala Asp Leu Val Ala
1               5                   10                  15

Lys Ala Asn Asp Arg Leu Pro Leu Ile Leu Glu Asp Ile Glu Arg Val
            20                  25                  30

Ile Thr Lys Glu Thr Pro Ser His Asp Lys Glu Ala Val Ala Ala Gly
        35                  40                  45

Ala Ala Asp Phe Val Glu Leu Leu Arg Glu Arg Leu Gly Ala Thr Ala
    50                  55                  60

Glu Val Ile Thr Val Asp Asp Thr Ala His Val Arg Leu Arg Phe Gly
65                  70                  75                  80

Ser Gly Pro Ala Arg Val Val Leu Leu Asn His Gln Asp Thr Val Trp
                85                  90                  95

Pro His Gly Thr Leu Asp Arg Ile Pro Phe Ser Thr Asp Asp Gly Ile
            100                 105                 110

Leu Arg Gly Pro Gly Ser Phe Asp Met Leu Thr Gly Ala Ile Met Ser
        115                 120                 125

Ile His Ala Ser Ala Ile Leu Arg Glu His Leu Gly Glu Gly Gly Leu
    130                 135                 140

Asp Gly Leu Ser Ile Leu Val Ser Gly Asp Glu Glu Ile Gly Ser Ile
145                 150                 155                 160

Ser Ser Ser Asp Leu Ile Arg Ala Glu Ala Ala Glu Ala Lys Ala Val
                165                 170                 175
```

Tyr Val Met Glu Ala Ser Ala Gly Gly Ala Leu Lys Leu Glu Arg Lys
            180                 185                 190

Gly Thr Ser Asn Tyr Val Leu Val Phe Thr Gly Lys Ala Ser His Ala
        195                 200                 205

Gly Leu Glu Pro Glu Lys Gly Ile Asn Ala Gly Met Ala Leu Ala Leu
    210                 215                 220

His Leu Pro Leu Val Ala Asp Leu Ala Asp Thr Glu Ala Gly Thr Ser
225                 230                 235                 240

Val Val Pro Thr Val Ile Ser Ala Gly Thr Thr Ser Asn Thr Val Pro
                245                 250                 255

Ala Glu Ala Arg Val Asp Ile Asp Val Arg Ala Arg Thr Ala Ala Glu
            260                 265                 270

Leu Asp Arg Val Asp Ala Ala Ile Arg Glu Leu Ala Thr Arg Pro Gln
        275                 280                 285

Leu Glu Gly Ser Ser Ile Glu Val Leu Gly Gly Ile Asn Arg Pro Pro
    290                 295                 300

Phe Glu Arg Glu Gln Ser Ala Val Leu Phe Glu Arg Ala Thr Ala Leu
305                 310                 315                 320

Ala Ala Glu Leu Gly Leu Pro Ala Pro Glu Gly Val Ser Val Gly Gly
                325                 330                 335

Ala Ser Asp Gly Asn Phe Thr Ala Gly Asp Gly Ile Ala Thr Leu Asp
            340                 345                 350

Gly Leu Gly Ala Val Gly Asp Gly Ala His Ala Glu His Glu His Ala
        355                 360                 365

Val Ile Asp Glu Ile Ala Pro Arg Thr Ala Leu Leu Ala Ala Leu Ile
    370                 375                 380

Ala Asp Gln Leu Gln Gly
385                 390

<210> SEQ ID NO 2
<211> LENGTH: 372
<212> TYPE: PRT
<213> ORGANISM: Brevibacterium linens

<400> SEQUENCE: 2

Met Val Glu Phe Asp Ser Lys Asp Phe Met Ser Asp Phe Lys Ala Leu
1               5                   10                  15

Ile Glu Cys Glu Ser Phe Ser Gln Asp Pro Glu Ser Leu Ala Arg Ser
            20                  25                  30

Ala Gln Leu Val Ser Arg Ile Gly Thr Gly Leu Leu Gly Ala Ala Pro
        35                  40                  45

His Ile Ile Glu Thr Asp Ser His Pro His Val Leu Trp Arg Phe Gly
    50                  55                  60

Thr Gly Pro Arg Lys Val Val Leu Ile Gly His His Asp Thr Val Trp
65                  70                  75                  80

Pro Thr Gly Thr Leu Ser Glu Phe Pro Tyr Ser Val Ala Asp Gly Val
                85                  90                  95

Val Arg Gly Pro Gly Ala Asp Asp Met Lys Gly Gly Leu Leu Ile Ala
            100                 105                 110

Leu Tyr Ala Met Ala Arg Leu Arg Glu Gln Arg Gly Asp Leu Ala Gly
        115                 120                 125

Val Ser Ile Leu Met Thr Gly Asp Glu Glu Leu Gly Ser Pro Gly Ser
    130                 135                 140

Arg Gln Ile Ile Glu Asp Glu Ala Arg Gly Ala Lys Ala Ala Leu Val

```
                145                 150                 155                 160
        Phe Glu Ser Gly Ala Pro Asp Gly Ala Val Lys Ile Ala Arg Lys Gly
                        165                 170                 175

Val Ala Ile Tyr Ser Leu Glu Val Thr Gly Leu Ala Ala His Ala Gly
                        180                 185                 190

Val Glu Pro Glu Lys Gly Ile Asn Ala Thr Ile Glu Val Ala Asn Gln
                        195                 200                 205

Val Val Lys Ile Ala Ala Leu His Asp Pro Ser Val Gly Thr Ser Val
                210                 215                 220

Val Pro Thr Val Met His Ser Gly Ser Thr Thr Asn Thr Val Pro Ala
        225                 230                 235                 240

Lys Ala Val Val Gly Val Asp Ser Arg Ala Ala Ser Val Ala Glu Gln
                        245                 250                 255

Glu Arg Ile Asp Ala Ile Leu Ser Asp Leu Ser Pro Thr Val Ala Gly
                        260                 265                 270

Ala Lys Val Asp Val Arg Gly Gly Ile Asn Arg Ala Pro Leu Glu Glu
                        275                 280                 285

Lys Met Ala Met Gly Leu Tyr Ala Arg Ala Gln Arg Leu Ser Ala His
                290                 295                 300

Leu Gly His Pro Pro Leu Arg Ser Val Ala Val Gly Gly Gly Ser Asp
        305                 310                 315                 320

Gly Asn Phe Thr Ala Gly Val Gly Thr Pro Thr Ile Asp Gly Leu Gly
                        325                 330                 335

Thr Val Gly Gly Gly Ser His Ala Arg Thr Glu His Ala Leu Gln Val
                        340                 345                 350

Trp Ile Pro Arg Arg Val Glu Leu Thr Thr Ala Leu Val Gly Glu Leu
                        355                 360                 365

Leu Ala Glu Asp
                        370

<210> SEQ ID NO 3
<211> LENGTH: 485
<212> TYPE: PRT
<213> ORGANISM: Brevibacterium linens

<400> SEQUENCE: 3

Met Asn Pro Thr Pro Glu Arg Lys Lys Ser Lys Arg Ser Lys Lys Ala
        1               5                   10                  15

Val Ala Gly Ile Thr Ala Gly Ser Leu Ala Val Leu Leu Ala Gly Val
                        20                  25                  30

Ala Ala Leu Asp Ala Tyr Asp Val Phe Pro Glu Leu Pro Gly Ile Leu
                        35                  40                  45

Thr Thr Glu Pro Ala Ile Glu Val Gln Asp Val Leu Ser Pro His Ala
                50                  55                  60

Gln Gly Lys Asp Val Pro Ala Pro Ala Ser Ala Leu Asp Asp Ser Ala
        65                  70                  75                  80

Pro Val Pro Thr Ala Ile Pro Asp Glu Val Asp Lys Val Leu Ser Asp
                        85                  90                  95

Ala Lys Val Lys Gly Phe Gly Ile Glu Ile Arg Asp Gly Leu Ser Asp
                        100                 105                 110

Asp Ile Leu Tyr Ala Lys Asn Glu Asn Lys Pro Arg Thr Pro Ala Ser
                        115                 120                 125

Val Thr Lys Val Leu Thr Gly Ser Ala Ala Leu Leu Thr Ile Gly Gly
                130                 135                 140
```

Glu Lys Arg Leu Ser Thr Thr Thr Gln Phe Asp Pro Ala Thr Ser Thr
145                 150                 155                 160

Val Thr Leu Gln Gly Gly Gly Asp Ser Leu Leu Gly Ala Gly Glu Ser
            165                 170                 175

Gln Pro Gly Ala Val Asn Gly His Ala Gly Leu Ala Thr Leu Ala Gln
            180                 185                 190

Gln Thr Ala Glu Ser Leu Lys Ser Gln Asn Val Ala Glu Val Ala Leu
            195                 200                 205

Asp Leu Asp Thr Ser Arg Tyr Ser Gly Lys Asp Phe Ser Pro Gly Trp
210                 215                 220

Glu Arg Val Asp Ile Ala Lys Gly Val Ile Thr Pro Ile Gln Pro Leu
225                 230                 235                 240

Met Ile Asp Thr Gly Tyr Val Gly Ser Lys Asp Lys Glu Trp Arg Gly
            245                 250                 255

Arg Ser Glu His Pro Ala Lys Asp Ala Phe Ala Val Phe Thr Lys Glu
            260                 265                 270

Leu Lys Ala Ala Gly Ile Thr Val Ser Lys Asp Pro Gln Pro Ala Asp
            275                 280                 285

Ala Thr Asp Ala Thr Gly Asp Glu Ala Lys Pro Thr Glu Leu Ala Glu
290                 295                 300

Val Glu Ser Ala Thr Ile Ser Glu Ile Val Glu Tyr Ala Leu Val His
305                 310                 315                 320

Ser Asp Asn Val Val Ala Glu Val Leu Gly Asn Glu Val Ala Ile Ala
            325                 330                 335

Gln Gly Glu Pro Gly Ser Leu Glu Ala Gly Pro Gln Ala Val Leu Asp
            340                 345                 350

Ala Leu Ser Asp Thr Val Asp Leu Gly Gln Thr His Leu Glu Asp Thr
            355                 360                 365

Ser Gly Leu Ser Tyr Asp Asn Gln Ile Ser Pro His Asp Leu Thr Thr
            370                 375                 380

Ile Leu Gln Ala Ser Val Val Ala Asp Asp Ser Leu Ser Asp Leu Ile
385                 390                 395                 400

Ala Ala Met Pro Val Gly Gly Leu Thr Gly Thr Leu Thr Asp Arg Phe
            405                 410                 415

Thr Lys Asp Arg Asn Ala Ala Gly Ala Val His Ala Lys Thr Gly Thr
            420                 425                 430

Leu Ser Thr Val Thr Ser Leu Ala Gly Gly Val Leu Asp Ala Asp Gly
            435                 440                 445

Arg Tyr Leu Val Phe Thr Leu Gln Ile Asp Val Asp Lys Asp Lys
450                 455                 460

Ile Leu Glu Ala Arg Lys Thr Val Asp Asp Ile Val Ala Ala Leu Ala
465                 470                 475                 480

Asn Cys Gly Cys Arg
            485

<210> SEQ ID NO 4
<211> LENGTH: 359
<212> TYPE: PRT
<213> ORGANISM: Brevibacterium linens

<400> SEQUENCE: 4

Met Asp Leu Phe Thr Asp Ser Ser His Thr Ala Leu Pro Ser Trp Leu
1               5                   10                  15

Arg Pro Val Pro Ala Thr Arg Arg Leu Arg Leu Leu Leu Ala Gly Ser
            20                  25                  30

Leu Leu Ala Leu Thr Phe Thr Val Ala Glu Val Gly Leu Pro Leu Glu
            35                  40                  45

Ser Pro Thr His Ile Ser Ser Ala Ala Ala Ala Thr Ser Thr Val Ala
 50                  55                  60

Ala Thr Ser Val Ser Glu Ala Glu Pro Thr Trp Val Ser Pro Val Pro
 65                  70                  75                  80

Ala Met Glu Ile Ile Glu Ala Phe Asp Pro Pro Thr Glu Ala Trp Leu
                85                  90                  95

Lys Gly His Arg Gly Ile Asp Val Leu Thr Val Ser Gly Glu Pro Val
                100                 105                 110

Arg Ala Pro Ala Ala Gly Thr Ile Arg Phe Arg Gly Thr Val Ala Gly
            115                 120                 125

Thr Ala Thr Val Ser Ile Val Thr Asp Ser Gly His Val Val Ser Phe
130                 135                 140

Gln Pro Ala Lys Ser Glu Leu Asn Lys Gly Arg Phe Ala Ala Gly
145                 150                 155                 160

Glu Glu Ile Gly Thr Val Gly Lys Gly Ser His Cys Asp Glu Ser Cys
                165                 170                 175

Leu His Ile Gly Val Trp Ala Ala Gln Gly Asp Lys Val Tyr Ile Asp
                180                 185                 190

Pro Ala Gly Phe Phe Gly Gln Glu Glu Ser Ile Leu Leu Pro Leu Ser
            195                 200                 205

Arg Lys Pro Ala Lys Glu Pro Thr Gly Asp Ser Thr Thr Ser Gly Ala
210                 215                 220

Gly Ala Trp Gly Gly His Arg Asn Gly Arg Ile Pro Ala Ala Ala Met
225                 230                 235                 240

Cys Thr Leu Asp Ser Ala Pro Gly Gln Met Leu Arg Cys Asp Ala Gln
                245                 250                 255

Lys Ala Phe Asp Arg Met Ser His Ala Tyr Glu Ala Arg Phe Ser Thr
            260                 265                 270

Pro Ile Ser Val Thr Asp Ala Tyr Arg Asp Tyr Asp Thr Gln Val Ile
        275                 280                 285

Leu Lys Lys Arg Lys Gly Arg Met Ala Ala Thr Pro Gly Thr Ser Asn
    290                 295                 300

His Gly Trp Ala Leu Ala Val Asp Leu Gly Gly Gly Ile Asn Ser Phe
305                 310                 315                 320

Gly Ser Ala Gln His Gln Trp Met Arg Ala Asn Ala Pro Lys Phe Gly
                325                 330                 335

Trp Ile His Pro Gly Trp Ala Arg Gln Ser Gly Ser Leu Pro Glu Pro
            340                 345                 350

Trp His Trp Glu Phe Arg Gln
        355

<210> SEQ ID NO 5
<211> LENGTH: 408
<212> TYPE: PRT
<213> ORGANISM: Brevibacterium linens

<400> SEQUENCE: 5

Met Arg Phe Thr Arg Ser Thr Ala Ser Ser Pro Arg Ala Ala Leu Leu
 1               5                  10                  15

Arg Val Leu Gly Phe Ala Ala Leu Leu Val Leu Pro Ala Gln Leu
             20                  25                  30

Val His Ser Pro Ala Pro Ala Gln Ala Val Pro Gln Pro Ala Glu Ser

```
                35                  40                  45
Thr Ala Pro Ala Tyr Val Ser Pro Asp Asp Leu Gly Asp Gly Ala Lys
 50                  55                  60
Pro Pro Lys Pro Thr Gly Thr Ser Trp Leu Val Gly Asp Leu Asp Ser
 65                  70                  75                  80
Gly Glu Leu His Val Ala Lys Asn Val Glu Lys Arg His Ala Pro Ala
                 85                  90                  95
Ser Thr Ile Lys Leu Leu Thr Ala Leu Ala Leu Val Asp Glu Phe Asp
                100                 105                 110
Asp Lys Lys Lys Val Thr Ala Glu Phe Glu Asp Met Glu Val Asp
        115                 120                 125
Gly Thr Lys Val Gly Leu Met Gln Thr Asn Lys Tyr Ser Ile Asp Leu
130                 135                 140
Leu Phe His Ala Met Leu Met Ser Ser Ala Asn Asp Ala Ala Asn Ala
145                 150                 155                 160
Leu Gly Arg Ala Ala Gly Gly Gln Asp Lys Ala Val Asp Leu Met Asn
                165                 170                 175
Glu Lys Ala Ala Glu Leu Gly Met Ser Asn Thr Gln Ala Lys Asn Thr
                180                 185                 190
Ser Gly Leu Asp Ala Lys Gly Gln Tyr Thr Thr Ala Glu Asp Leu Met
                195                 200                 205
Lys Leu Ala Trp Ala Val Cys Glu Asp Asp Tyr Leu Met Lys Val Ile
210                 215                 220
Gly Thr Glu Thr Tyr Gln Phe Pro Gly Gly Thr Asn Pro Glu Thr Lys
225                 230                 235                 240
Glu Lys Phe Lys Gly Tyr Glu Ile Gln Asn His Thr Lys Ile Ala Gly
                245                 250                 255
Gln Val Asp Gly Gly Leu Gly Leu Lys Asn Gly Phe Thr Arg Ala Ala
                260                 265                 270
Lys Gly Ser Tyr Val Ala Val Ala Glu Arg Asp Gly His Arg Val Val
                275                 280                 285
Ala Thr Met Leu Gly Ile Asp Asn Asn Ser Arg Gln Ala Ala Val Asp
290                 295                 300
Leu Leu Glu Trp Asp Phe Ala Gln Thr Asp Pro Lys Ser Leu Gln Thr
305                 310                 315                 320
Val Pro Val Gly Val Gln Ala Thr Ala Glu Ala Val Pro Thr Ala Thr
                325                 330                 335
Gly Ser Ser Ser Asp Ala Gly Gly Ala Asp Ser Asp Ala Ser Gly Ala
                340                 345                 350
Ala Glu Ser Lys Val Thr Asp Glu Ser Glu Pro Ser Met Ala Ala Gln
                355                 360                 365
Thr Leu Gly Ala Ala Leu Asp Asn Pro Leu Ala Leu Gly Leu Leu Ala
370                 375                 380
Gly Gly Val Val Leu Phe Val Leu Thr Val Val Leu Trp Ala Arg Leu
385                 390                 395                 400
Arg Ala Arg Met Gln Gly Arg Arg
                405

<210> SEQ ID NO 6
<211> LENGTH: 389
<212> TYPE: PRT
<213> ORGANISM: Brevibacterium linens

<400> SEQUENCE: 6
```

```
Met Ile Ser Ser Thr Ile Ala Glu Ile Gly Ala Glu Leu Ile Asp Phe
1               5                   10                  15

Arg Arg Asp Val His Ala His Pro Glu Leu Ser Phe Gln Glu Phe Gly
            20                  25                  30

Thr Thr Asp Lys Ile Val Ala Arg Leu Glu Ala Ala Gly Leu Ser Pro
            35                  40                  45

Arg Arg Leu Glu Ser Thr Gly Val Val Cys Glu Val Gly Glu Gly Pro
50                  55                  60

Leu Ala Leu Gly Leu Arg Ala Asp Ile Asp Ala Leu Pro Ile Asp Asp
65                  70                  75                  80

Leu Ile Asp Glu Asp Phe Ala Ser Thr Val Pro Gly Val Ala His Ala
            85                  90                  95

Cys Gly His Asp Val His Leu Thr Gly Leu Val Gly Ala Ala Ile Ala
            100                 105                 110

Leu Gln Arg Leu His Glu Ser Thr Pro Gly Gly Leu Gly Gly Arg Val
            115                 120                 125

Arg Leu Ile Phe Gln Pro Gly Glu Glu Val Thr Pro Gly Gly Ala Leu
            130                 135                 140

Arg Val Ile Ser Gln Gly Val Leu Asp Asp Val Pro Glu Val Tyr Ala
145                 150                 155                 160

Leu His Cys Asp Pro Asn Val Asp Val Gly Lys Ile Gly Ser Arg Ile
            165                 170                 175

Gly Ala Ile Thr Ala Ala Gly Asp Thr Val Ile Arg Leu Ser Gly
            180                 185                 190

His Gly Gly His Thr Ser Arg Pro His Leu Thr Glu Asp Leu Val Tyr
            195                 200                 205

Ala Leu Gly Lys Leu Ala Thr Asp Leu Pro Ser Thr Leu Gly Arg Leu
            210                 215                 220

Ile Asp Pro Arg His Ala Ile Ser Leu Val Trp Gly Glu Ile Ser Ala
225                 230                 235                 240

Gly His Ala Ala Asn Val Val Pro Ser Glu Gly Ile Leu Arg Gly Thr
            245                 250                 255

Leu Arg Cys Leu Asp Val Asp Gly Trp Asn Gln Val Ala Glu Val Leu
            260                 265                 270

Pro Glu Leu Val Glu Arg Ile Ala Gly Pro Tyr Gly Val Thr Val Asp
            275                 280                 285

Leu Asp His Arg Arg Gly Val Pro Pro Val Val Asn Thr Glu Asp Gln
            290                 295                 300

Val Ala Leu Ile Glu Ser Ala Val Arg Gly Glu Leu Gly Glu Asn Ser
305                 310                 315                 320

Val Gln Leu Thr Pro Gln Ser Met Gly Gly Glu Asp Phe Ala Trp Tyr
            325                 330                 335

Leu Thr His Cys Pro Gly Ala Leu Val Arg Met Gly Thr Arg Thr Pro
            340                 345                 350

Gly Gly Lys Thr Tyr Asp Ile His Gln Gly Asp Leu Leu Ile Asp Glu
            355                 360                 365

Asp Ser Val Glu Ile Ala Ala Arg Ile Phe Thr Ala Thr Ala Leu Lys
            370                 375                 380

Val Leu Gln Arg Asp
385
```